US012779123B2

(12) United States Patent
Carlsson

(10) Patent No.: US 12,779,123 B2
(45) Date of Patent: Nov. 3, 2026

(54) MEDICAMENT DELIVERY DEVICE

(71) Applicant: SHL MEDICAL AG, Zug (CH)

(72) Inventor: Daniel Carlsson, Enskede (SE)

(73) Assignee: SHL Medical AG, Zug (CH)

( * ) Notice: Subject to any disclaimer, the term of this patent is extended or adjusted under 35 U.S.C. 154(b) by 595 days.

(21) Appl. No.: 18/278,701

(22) PCT Filed: Dec. 21, 2021

(86) PCT No.: PCT/EP2021/086919

§ 371 (c)(1),
(2) Date: Aug. 24, 2023

(87) PCT Pub. No.: WO2022/207136

PCT Pub. Date: Oct. 6, 2022

(65) Prior Publication Data

US 2024/0139416 A1 May 2, 2024

(30) Foreign Application Priority Data

Mar. 31, 2021 (EP) .................................... 21166428

(51) Int. Cl.
*A61M 5/20* (2006.01)
*A61M 5/28* (2006.01)
(Continued)

(52) U.S. Cl.
CPC ........ *A61M 5/2053* (2013.01); *A61M 5/2033* (2013.01); *A61M 5/282* (2013.01); (Continued)

(58) Field of Classification Search
CPC ............................ A61M 5/2053; A61M 5/282
See application file for complete search history.

(56) References Cited

U.S. PATENT DOCUMENTS 4,019,655 A 4/1977 Moeller
6,808,507 B2 10/2004 Roser
(Continued)

FOREIGN PATENT DOCUMENTS

CN 111225699 A 6/2020
EP 4137182 A1 * 2/2023 .......... A61M 5/3202
(Continued)

OTHER PUBLICATIONS

International Search Report and Written Opinion for Int. App. No. PCT/EP2021/086919, mailed Feb. 10, 2022.

*Primary Examiner* — Michael J Tsai
(74) *Attorney, Agent, or Firm* — McDonnell Boehnen Hulbert & Berghoff LLP

(57) ABSTRACT

A medicament delivery device is presented having a mechanically flexible medicament container structure contained in a housing having a proximal end and a distal end, a hinge structure having two hinge arms, the hinge structure being arranged in the housing and configured to receive a portion of the medicament container structure between the two hinge arms, and a hollow drive member biased towards the proximal end and arranged distally relative to the hinge arms in the housing the drive member having an inner diameter which is smaller than a radial dimension of the hinge arms, wherein the drive member is configured to be released from a first axial position during a medicament delivery operation and move towards the proximal end of the housing, causing the drive member to move radially over the hinge arms which thereby move radially inwards towards each other to mechanically deform the portion of the medicament container structure for expulsion of medicament.

17 Claims, 5 Drawing Sheets

(51) Int. Cl.
*A61M 5/32* (2006.01)
*A61M 5/50* (2006.01)

(52) U.S. Cl.
CPC .......... *A61M 5/3234* (2013.01); *A61M 5/326* (2013.01); *A61M 5/5086* (2013.01); *A61M 2005/2013* (2013.01); *A61M 2005/3267* (2013.01)

(56) References Cited

U.S. PATENT DOCUMENTS

| | | | | |
|---|---|---|---|---|
| 9,033,935 | B2 * | 5/2015 | Bostrom | A61M 5/2033 604/198 |
| 9,821,116 | B2 | 11/2017 | Vouillamoz et al. | |
| 10,155,088 | B2 | 12/2018 | Basile | |
| 10,500,338 | B2 | 12/2019 | Berenshteyn | |
| 10,716,901 | B2 * | 7/2020 | Genosar | A61M 5/2066 |
| 12,377,221 | B2 * | 8/2025 | Maxfield | A61M 5/2466 |
| 2003/0212362 | A1 | 11/2003 | Roser | |
| 2009/0311030 | A1 * | 12/2009 | Stenton | A61B 17/00491 401/165 |
| 2010/0137808 | A1 | 6/2010 | Wilmot et al. | |
| 2014/0046270 | A1 | 2/2014 | Thornton | |
| 2014/0081239 | A1 * | 3/2014 | Cronenberg | A61M 5/5066 604/110 |
| 2014/0296782 | A1 * | 10/2014 | Ulrich | A61M 5/158 604/173 |
| 2015/0165123 | A1 * | 6/2015 | Thornton | A61M 5/282 604/110 |
| 2015/0209519 | A1 | 7/2015 | Mernoe | |
| 2016/0074586 | A1 | 3/2016 | Mernøe et al. | |
| 2016/0361496 | A1 * | 12/2016 | Guillermo | A61M 5/2046 |
| 2017/0080153 | A1 | 3/2017 | Maxfield | |
| 2018/0028756 | A1 * | 2/2018 | Maxfield | A61M 5/3202 |
| 2018/0104418 | A1 * | 4/2018 | Berenshteyn | A61M 5/2425 |
| 2019/0060579 | A1 * | 2/2019 | Daniel | A61M 5/3202 |
| 2020/0179607 | A1 * | 6/2020 | Judson | A61M 5/3158 |
| 2020/0345937 | A1 | 11/2020 | Genosar | |
| 2021/0402097 | A1 * | 12/2021 | Genosar | A61M 5/32 |
| 2022/0040413 | A1 * | 2/2022 | Edwards | A61M 5/2046 |
| 2022/0215779 | A1 * | 7/2022 | Yin | A61M 5/3157 |
| 2022/0323695 | A1 * | 10/2022 | Albertini | G16H 70/40 |
| 2024/0009395 | A1 * | 1/2024 | Koska | A61M 5/282 |
| 2024/0017020 | A1 * | 1/2024 | Säll | A61M 5/2425 |
| 2024/0139416 | A1 * | 5/2024 | Carlsson | A61M 5/3234 |

FOREIGN PATENT DOCUMENTS

| | | | | |
|---|---|---|---|---|
| WO | WO-2010147553 | A1 * | 12/2010 | A61M 5/24 |
| WO | 2012/93075 | A1 | 7/2012 | |
| WO | 2014/177160 | A1 | 11/2014 | |
| WO | WO-2021155981 | A1 * | 8/2021 | A61M 5/31545 |
| WO | WO-2023031000 | A1 * | 3/2023 | A61M 5/3204 |

* cited by examiner

MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2021/086919 filed Dec. 21, 2021, which claims priority to European Patent Application No. 21166428.9 filed Mar. 31, 2021. The entire disclosure contents of these applications are herewith incorporated by reference into the present application.

TECHNICAL FIELD

The present disclosure generally relates to a medicament delivery device for expelling medicament from a flexible medicament container.

BACKGROUND

Some liquid chambers may be mechanically flexible or soft. A blow-fill-seal (BFS) container is an example of a common type of flexible container containing liquid.

Today, BFS containers filled with a medicament are typically handled manually by the user during administration. This means that the user has to compress the liquid chamber or the gas-filled chamber manually to expel the medicament from the BGF container. This is typically done by medical professionals to ensure that the dose is administered correctly.

US2003/0212362 A1 discloses an injector device configured to discharge the content of a plastic blister Uniject™ device. The injector device has a cap and a barrel configured to slide relative to the cap. A shaped plastic moulding is used to enclose the Uniject™ device in the injection device. During assembly, the shaped plastic moulding is folded around the Uniject™ device. In use, a distal free end of the device is pressed against the skin of the patient. The cap is then able to slide telescopically over the barrel causing inner tabs of the injection device to break. The shaped plastic moulding eventually slides over the Uniject™ device, until its dome contacts, and presses on, the blister. The content of the blister is thus discharged into the subcutaneous tissue or muscle layer.

The injection relies on the interaction as the shaped plastic moulding slides in the barrel and presses against the blister of the Uniject™ device. The controllability of the injection is therefore relatively low, and the blister may thus not be fully emptied.

SUMMARY

An object of the present disclosure is thus to provide a medicament delivery device which solves, or at least mitigates, problems of the prior art.

There is hence according to a first aspect of the present disclosure provided a medicament delivery device for expelling medicament from a mechanically flexible medicament container structure, the medicament delivery device comprising: a housing having a proximal end and a distal end, a hinge structure having two hinge arms, the hinge structure being arranged in the housing and configured to receive a portion of the medicament container structure between the two hinge arms, and a hollow drive member biased towards the proximal end and arranged distally relative to the hinge arms in the housing, the drive member having an inner diameter which is smaller than a radial dimension of the hinge arms, wherein the drive member is configured to be released from a first axial position during a medicament delivery operation and move towards the proximal end of the housing, causing the drive member to move radially over the hinge arms which thereby move radially inwards towards each other to mechanically deform the portion of the medicament container structure for expulsion of medicament.

An effect obtainable thereby is that improved control of medicament discharging may be provided.

In the present disclosure, when the term “distal direction” is used, this refers to the direction pointing away from the dose delivery site during use of the medicament delivery device. When the term “distal part/end” is used, this refers to the part/end of the delivery device, or the parts/ends of the components thereof, which under use of the medicament delivery device is/are located furthest away from the dose delivery site. Correspondingly, when the term “proximal direction” is used, this refers to the direction pointing towards the dose delivery site during use of the medicament delivery device. When the term “proximal part/end” is used, this refers to the part/end of the delivery device, or the parts/ends of the members thereof, which under use of the medicament delivery device is/are located closest to the dose delivery site.

Further, the term “longitudinal”, “longitudinally”, “axially” or “axial” refer to a direction extending from the proximal end to the distal end, typically along the device or components thereof in the direction of the longest extension of the device and/or component.

Similarly, the terms “transverse”, “transversal” and “transversally” refer to a direction generally perpendicular to the longitudinal direction.

Further, the terms “circumference”, “circumferential”, “circumferentially” refer to a circumference or a circumferential direction relative to an axis, typically a central axis extending in the direction of the longest extension of the device and/or component. Similarly, “radial” or “radially” refer to a direction extending radially relative to the axis, and “rotation”, “rotational” and “rotationally” refer to rotation relative to the axis.

According to one embodiment the hinge arms are directed towards the proximal end of the housing. The hinge arms thus extend towards the proximal end of the housing.

According to one embodiment each hinge arm has an end portion that tapers in a direction towards the distal end of the housing. The end portion may for example have the shape of a ramp directed towards the distal end of the housing.

According to one embodiment the hinge structure is biased towards the distal end of the housing, and wherein the hinge structure has a frame provided with radially outwards extending protrusions configured to bear against a proximal end of the drive member for distancing the hinge arms from contact with the drive member when the drive member is in the first axial position.

The hinge structure may thereby be provided in a fixed axial position, in which the hinge arms do not interact with the drive member prior to medicament delivery.

One embodiment comprises a distal resilient member configured to bias the drive member towards the proximal end of the housing.

According to one embodiment the mechanically flexible medicament container structure is a blow-fill-seal container.

There is according to a second aspect of the present disclosure provided a medicament delivery device for expelling medicament from a mechanically flexible medicament container structure having a proximal liquid container and a distal gas container in fluid communication with the liquid container, the medicament delivery device comprising: a housing having a proximal end and a distal end, a liquid container holder biased towards the distal end, the liquid container holder having a chamber configured to receive the liquid container, the liquid container holder having oppositely arranged radially flexible arms forming part of a respective side surface of the chamber, each arm having a radially outwards extending structure, an expulsion member configured to pressurise the gas container during a medicament delivery operation such that gas is expelled from the gas container into the liquid container to thereby expel liquid from the liquid container, and a holding sleeve arranged around the liquid container holder and being axially fixed relative to the housing, wherein the radially outwards extending structures are configured to be in contact with a respective radial surface of the holding sleeve to prevent the liquid container holder to move axially towards the distal end, wherein the arms are urged radially inwards against the liquid container by the biasing and the contact with the radial surfaces of the holding sleeve, wherein the arms are subjected to a radially outwards directed counterpressure by the liquid container when the liquid container is filled with liquid, and wherein the arms are configured to move radially inwards when the liquid container is emptied and its internal pressure is reduced, causing the radially outwards extending structures to be released from contact with the radial surfaces of the holding sleeve and the liquid container holder to move towards the distal end inside the housing and obtain a final axial position.

An indication that the medicament delivery has been completed may thereby be provided to the user. In particular, the user may be made aware of the end of delivery because the liquid container holder moves further into the housing.

Typically, the mechanically flexible medicament container structure, provided with a delivery member such as a needle, will also follow the distal movement of the liquid container holder because the liquid container is fixedly arranged in the liquid container holder. The delivery member may for example be moved fully into the housing.

According to one embodiment the radially outwards extending structures and/or the radial surfaces define inclined surfaces relative to a radial plane of the housing to facilitate radial inwards movement of the arms.

According to one embodiment the holding sleeve comprises radial openings, wherein each radial surface is formed by a distal end surface of a respective opening.

One embodiment comprises a proximal sleeve, and a proximal resilient member biasing the proximal sleeve against the liquid container holder in a direction towards the distal end of the housing, thereby biasing the liquid container holder towards the distal end of the housing.

One embodiment comprises a hinge structure having two hinge arms, the hinge structure being arranged in the housing and configured to receive the gas container between the two hinge arms, wherein the liquid container holder forms a proximal end of the hinge structure, wherein the expulsion member is a hollow drive member biased towards the proximal end and arranged distally relative to the hinge arms in the housing, the drive member having an inner diameter which is smaller than a radial dimension of the hinge arms, wherein the drive member is configured to be released from a first axial position during a medicament delivery operation and move towards the proximal end of the housing, causing the drive member to move radially over the hinge arms which thereby move radially inwards towards each other to mechanically deform the gas container.

According to one embodiment the hinge structure has a radially flexible frame provided with radially outwards extending protrusions configured to bear against a proximal end of the drive member for distancing the hinge arms from contact with the drive member when the drive member is in the first axial position, the drive member having radial openings configured to interlock with a respective one of the protrusions when the liquid container holder has reached its final axial position.

According to one embodiment the mechanically flexible medicament container structure is a blow-fill-seal container.

Generally, all terms used in the claims are to be interpreted according to their ordinary meaning in the technical field, unless explicitly defined otherwise herein. All references to “a/an/the member, apparatus, component, means, etc.” are to be interpreted openly as referring to at least one instance of the member, apparatus, component, means, etc., unless explicitly stated otherwise.

BRIEF DESCRIPTION OF THE DRAWINGS

The specific embodiments of the presently disclosed concept will now be described, by way of example, with reference to the accompanying drawings, in which.

DETAILED DESCRIPTION

The presently disclosed concept will now be described more fully hereinafter with reference to the accompanying drawings, in which exemplifying embodiments are shown. The presently disclosed concept may, however, be embodied in many different forms and should not be construed as limited to the embodiments set forth herein; rather, these embodiments are provided by way of example so that this disclosure will be thorough and complete, and will fully convey the scope of the presently disclosed concept to those skilled in the art. Like numbers refer to like members throughout the description.

Figure 1:
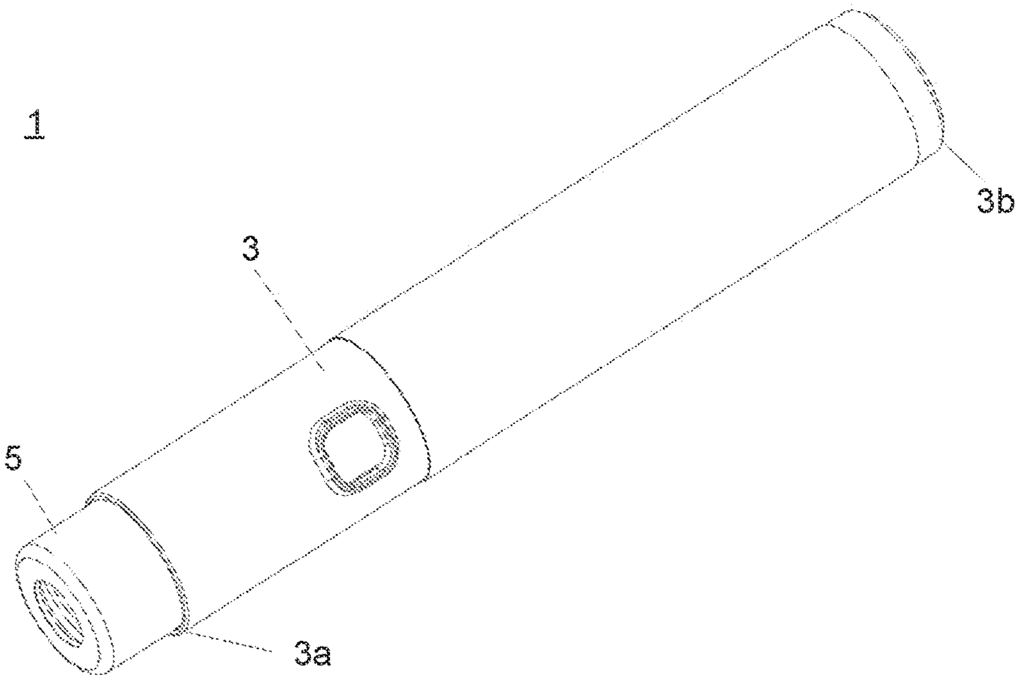
FIG. 1 schematically shows a perspective view of an example of a medicament delivery device.

FIG. 1 shows an example of a medicament delivery device 1 configured to expel medicament from a mechanically flexible medicament container structure. The mechanically flexible medicament container structure may for example be a BFS container.

The medicament delivery device 1 comprises a housing 3. The housing 3 has a proximal end 3*a* and a distal end 3*b*.

The medicament delivery device 1 comprises a delivery member cover 5. The delivery member cover 5 is arranged in the housing 3 and extends proximally from the proximal end 3*a*.

The delivery member cover 5 is configured to be moved linearly relative to the housing 3 from a first position shown in FIG. 1 to a second position in which the delivery member cover 5 is received further in the housing 3.

The delivery member cover 5 is biased in the proximal direction towards the first position.

The medicament delivery device 1 is triggered to discharge medicament by movement of the delivery member cover 5 further into the housing 3 towards the second position.

Figure 2:
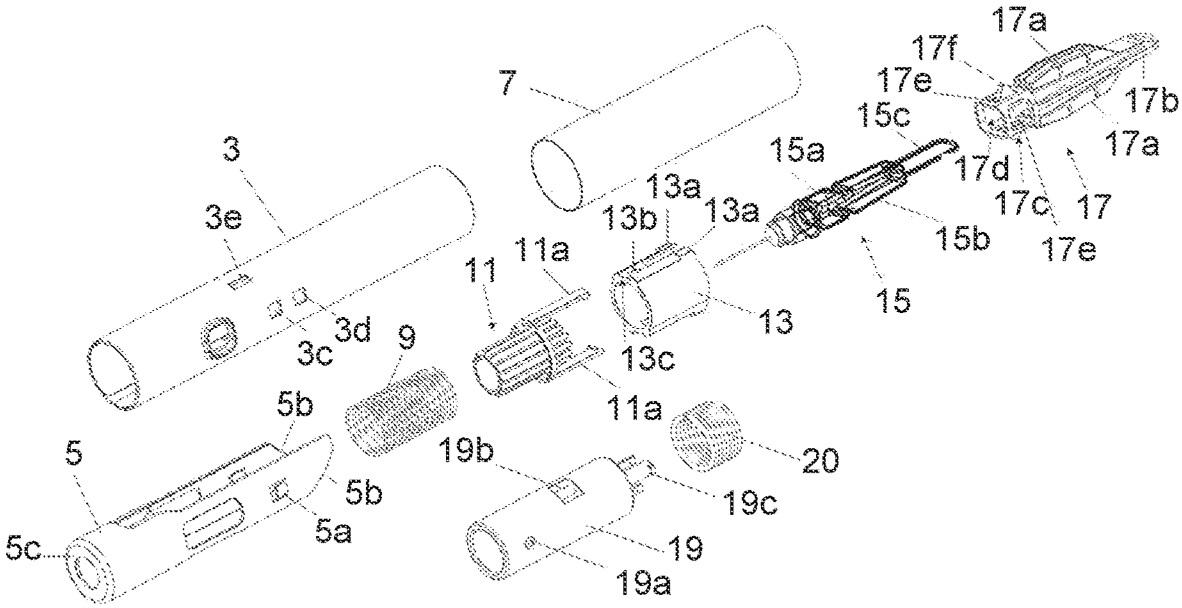
FIG. 2 shows an exploded view of the medicament delivery device in FIG. 1.

FIG. 2 shows an exploded view of the medicament delivery device 1.

The housing 3 is provided with a first radial opening 3*c* and a second radial opening 3*d*. The first radial opening 3*c* is arranged proximally relative to the second radial opening 3*d*. The first radial opening 3*c* and the second radial opening 3*d* are axially aligned.

The medicament delivery device 1 may comprise a housing sleeve 7 configured to cover at least a portion of the housing 3. The housing sleeve 7 may for example cover the first radial opening 3*c* and the second radial opening 3*d*.

The delivery member cover 5 comprises a radially flexible and radially outwards extending attachment member 5*a*, such as a tab, configured to engage with the first radial opening 3*c* when the delivery member cover 5 is in the first position.

The attachment member 5*a* is inclined and presents a decreasing ramp surface in the distal direction and can thereby flex radially inwards and disengage from the first radial opening 3*c* when the delivery member cover 5 is subjected to an axial force in the distal direction larger than a threshold value.

The attachment member 5*a* is configured to engage with the second radial opening 3*c* when the delivery member cover 5 is in the second position. The delivery member cover 5 is thereby interlocked with the housing 3 in the second position. The delivery member cover 5 is thus in this example not able to return to the first position from the second position.

The delivery member cover 5 has distal ends, each forming a cam surface 5*b*.

The medicament delivery device 1 comprises a proximal resilient member 9 configured to bear against an inner surface of a proximal end 5*c* of the delivery member cover 5. The proximal resilient member 9 may be a spring such as a coil spring.

The medicament delivery device 1 comprises a proximal sleeve 11. The proximal sleeve 11 is configured to be moved linearly relative to the housing 3. The proximal sleeve 11 is biased in the distal direction by the proximal resilient member 9. The distal end of the proximal resilient member 9 may for example bear directly against a proximal radial surface of the proximal sleeve 11.

According to the example shown in FIG. 2, the proximal sleeve 11 comprises guide arms 11*a* extending in the distal direction towards the distal end 3*b* of the housing 3.

The medicament delivery device 1 comprises a holding sleeve 13. The holding sleeve 13 is configured to engage with the housing 3. The holding sleeve 13 is axially and rotationally fixed relative to the housing 3. The holding sleeve 13 comprises radially outwards extending structures 13*a* configured to engage with a respective third radial opening 3*e* of the housing 3 for fixing the holding sleeve 13 to the housing 13.

The holding sleeve 13 comprises radial openings 13*b*. Each radial opening 13*b* has a distal end surface which is a radial surface.

The proximal sleeve 11 is configured to bear against the holding sleeve 13. The proximal sleeve 11 is configured to move axially in the distal direction relative to the holding sleeve 13.

The holding sleeve 13 comprises axial grooves 13*c* configured to receive a respective one of the guide arms 11*a*. The guide arms 11*a* are configured to move in the axial grooves 13*c* when the proximal sleeve 11 is moved in the distal direction.

The medicament delivery device 1 can be loaded with a mechanically flexible medicament container structure 15. The medicament container structure 15 comprises a proximal liquid container 15*a* and a distal gas container 15*b*. The liquid container 15*a* is arranged proximally relative to the distal gas container 15*b*. The gas container 15*b* is in fluid communication with the liquid container 15*a*. The liquid container 15*a* may comprise a liquid medicament. The gas container 15*b* may for example comprise air or an inert gas.

The container structure 15 may also comprise a planar end portion 15*c* arranged distally relative to the distal gas container 15*b*.

The medicament delivery device 1 comprises a hinge structure 17. The hinge structure 17 comprises two oppositely arranged hinge arms 17*a*. The hinge arms 17*a* are hingedly connected via a joint 17*b*. The hinge arms 17*a* extend in the proximal direction towards the proximal end 3*a* of the housing 3.

The hinge structure 17 is configured to receive a portion of the medicament container structure 15 between the two hinge arms 17*a*. According to the present example, the gas container 15*b* is configured to be arranged between the two hinge arms 17*a*.

The hinge arms 17*a* are inclined in relation to a radial plane, and thus extend radially outwards and away from each other in the proximal direction, when the distal gas container 15*b* is provided between the hinge arms 17*a* before use.

The hinge structure 17 may for example be made of a single integral piece of a polymeric material.

The hinge structure 17 comprises a liquid container holder 17*c*. The liquid container holder 17*c* is arranged proximally relative to the two hinge arms 17*a*. The liquid container 15*a* is configured to be arranged in the liquid container holder 17*c*. In particular, the liquid container holder 17*c* has a chamber 17*d* configured to receive the liquid container 15*a*. The liquid container 15*a* is typically arranged axially fixed relative to the liquid container holder 17*c*.

The liquid container holder 17*c* has oppositely arranged radially flexible arms 17*e* forming part of a respective side surface of the chamber 17*d*. Each arm 17*e* has a radially outwards extending structure 17*f*. The radially outwards extending structures 17*f* are configured to engage with a respective one of the radial openings 13*b* of the holding sleeve 13. The hinge structure 17 is thus axially locked to the holding sleeve 13. The holding sleeve 13, in turn, is axially fixed relative to the housing 3. The hinge structure 17 is thus fixed axially relative to the housing.

Each radially outwards extending structure 17*f* may have an inclined surface configured to cooperate with a respective radial surface of the holding sleeve 13. The inclined surfaces may for example have a ramp shape with a decreasing inclination in the distal direction.

The medicament delivery device 1 comprises a hollow drive member or expulsion member 19. The drive member 19 may have a cylindrical body. The drive member 19 is configured to be moved axially inside the housing 3. During a medicament delivery operation, the drive member 19 is configured to be moved from a first axial position towards the proximal end 3*a* of the housing 3.

The drive member 19 has an inner diameter which is smaller than a radial dimension of the hinge arms 17*a*. The radial dimension of the hinge arms 17*a* is defined by the largest radial distance between the outer surfaces of two the oppositely arranged hinge arms 17*a*.

When the delivery member cover 5 is in the first position, the drive member 19 is arranged distally relative to the two hinge arms 17*a*, in the first axial position.

The drive member 19 is biased in the proximal direction. The drive member 19 is axially fixed relative to the housing 3, in the first axial position, when the delivery member cover 5 is in the first position.

The drive member 19 may have a locking member 19*c* configured to engage with the housing 3 when the delivery member cover 5 is in the first position.

The delivery member cover 5 is configured to cooperate with the drive member 19. When the delivery member cover 5 is moved from the first position towards the second position, linear movement of the delivery member cover 5 is transformed into rotational movement of the drive member 19. This causes the drive member 19 to be released from engagement with the housing 3, and to move in the proximal direction. The hinge arms 17*a* are thereby moved radially inwards by the drive member 19, mechanically deforming the gas container 15*b*, as will be explained in more detail in the following.

The drive member 19*a* may comprise radially outwards extending protrusions 19*a* configured to cooperate with a respective one of the cam surfaces 5*b* to achieve rotation of the drive member 19*a* from an initial rotational position to a final rotational position as the delivery member cover 5 is moved from the first position to the second position.

The drive member 19 may for example have a distal end portion, wherein the distal end portion is provided with the locking member 19*c*. The locking member 19*c* may for example have two oppositely extending radial structures which when the drive member 19 is in the first rotational position are held by the housing 3 and which disengage from the housing 3 when the drive member 19 is rotated.

The medicament delivery device 1 comprises a distal resilient member 20. The distal resilient member 20 may for example be a spring, such as a coil spring. The distal resilient member 20 is configured to bias the drive member 19 in the proximal direction.

The drive member 19 has radial openings 19*b*. The radial openings 19*b* are provided in the cylindrical body of the drive member 19.

Figure 3A:
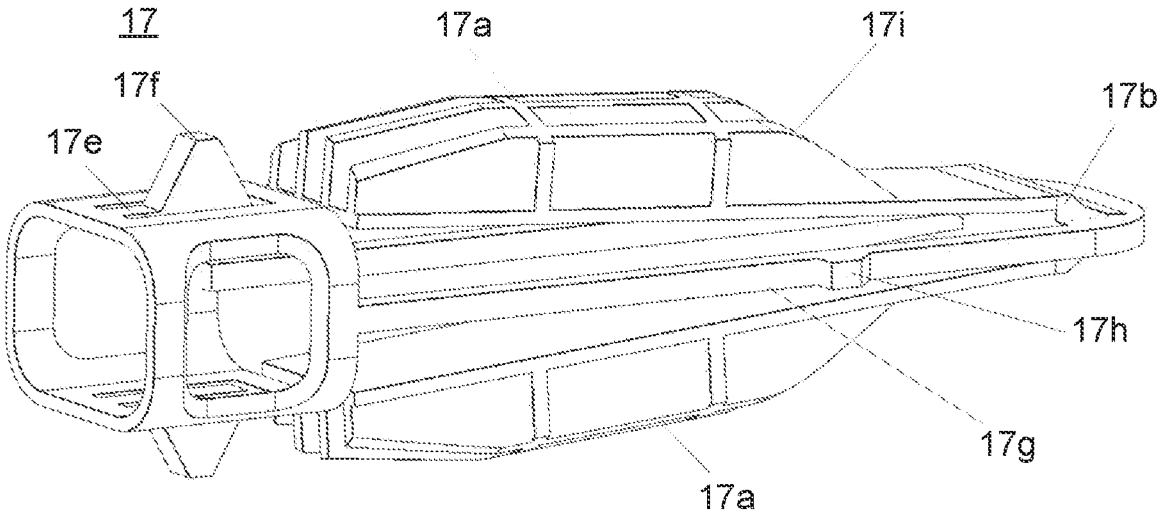
FIGS. 3A-3B show a perspective view and a top view, respectively, of a hinge structure of the medicament delivery device in FIG. 2.
Figure 3B:
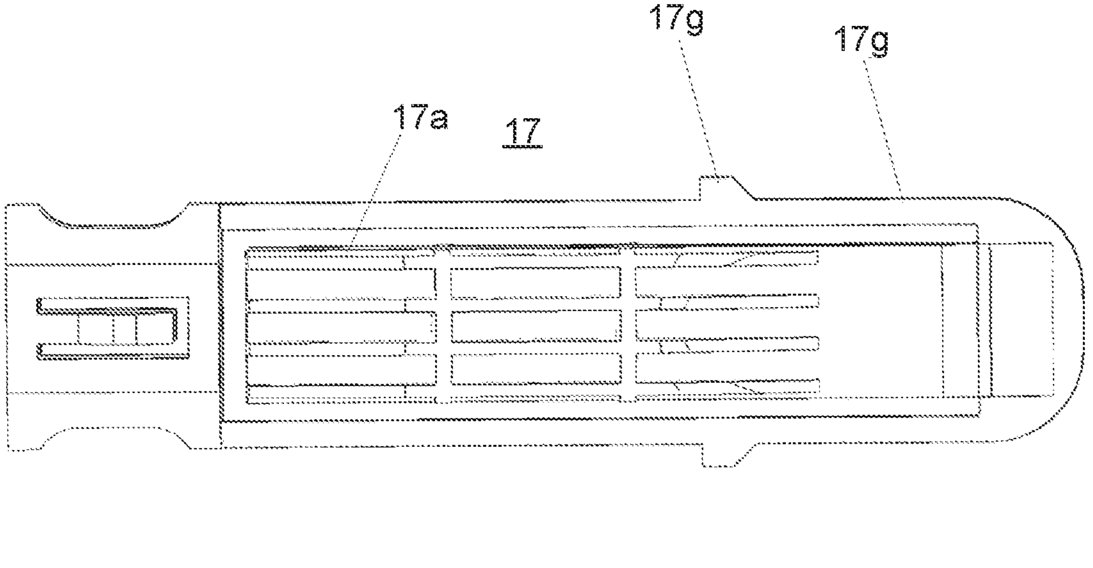

FIG. 3A shows a perspective view and FIG. 3B shows a top view of the hinge structure 17 in more detail. Each hinge arm 17*a* has an end portion 17*i* which tapers in the distal direction. The hinge arms 17*a* thus have a ramp shape, which increase in radial thickness in the proximal direction. When the drive member 19 is moved from the first axial position, its inner surface slides over the end portions 17*i*, causing the hinge arms 17*a* to be moved radially inwards towards each other as will be explained in more detail in the following.

The hinge structure 17 has a mechanically flexible frame 17*g*. The frame 17*g* is flexible radially. The frame 17*g* is provided with radially outwards extending protrusions 17*h*. The protrusions 17*h* are configured to bear against a proximal end of the drive member 19 for distancing the hinge arms 17*a* from contact with the drive member 18 when the drive member 19 is in the first axial position. The protrusions 17*h* have a ramp shape, increasing in radial thickness in the proximal direction.

When the drive member 19 is released from engagement with the housing 3, the frame 17*g* is flexed radially inwards and the hinge structure 17 is further received by the drive member 19. When the drive member 19 has moved in the proximal direction such that the radial openings 19*b* align axially with the protrusions 17*h*, the protrusions 17*h* are received by a respective one of the radial openings 19*b*. The hinge structure 17 is thereby interlocked with the drive member 19.

The operation of the medicament delivery device 1 will now be described in more detail with reference to FIGS. 4A-7.

Figure 4A:
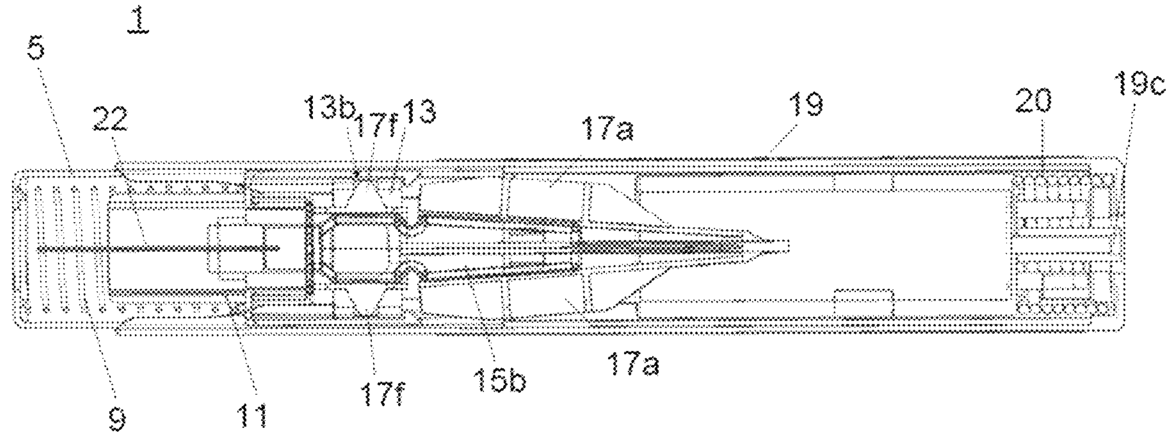
FIG. 4A is a sectional view of the medicament delivery device in a default state.

FIG. 4A shows a sectional view of the medicament delivery device 1 in a default state before medicament delivery.

The delivery member cover 5 is in the first position, biased in the proximal direction by the proximal resilient member 9. The delivery member cover 5 covers the delivery member 22 of the medicament container structure 15.

The radially outwards extending structures 17*f* of the arms 17*e* are arranged in a respective radial opening 13*b* of the holding sleeve 13. The holding sleeve 13 engages with the housing 3 and is axially fixed relative to the housing 3. The proximal sleeve 11, which bears against the holding sleeve 13 and which is distally biased by the proximal resilient member 9 is thus arranged axially fixed and so is the hinge structure 17.

The gas container 15*b* is arranged between the hinge arms 17*a*. Moreover, the drive member 19 is arranged in the first axial position distally relative to the tapering end portions of the hinge arms 17*a*. The drive member 19 engages with the housing 3. In the example, the locking member 19*c* engages with a distal end of the housing 3. The distal resilient member 20 is arranged distally relative to the hollow cylindrical body of the drive member 19, biasing the drive member 19 in the proximal direction.

Figure 4B:
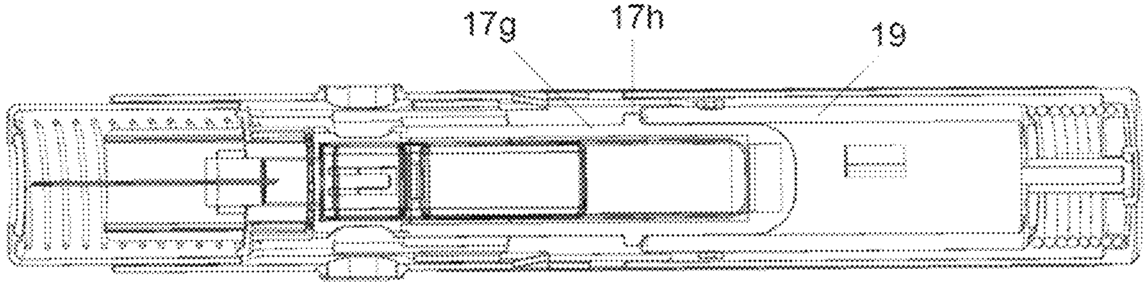
FIG. 4B is a sectional view of the medicament delivery device in the default state, the section being taken at 90 degrees angle relative to the section shown in FIG. 4A.

FIG. 4B shows a sectional view in a plane at 90 degrees angle relative to the sectional view shown in FIG. 4A. It can be seen that the protrusions 17*h* bear against a proximal end of the drive member 19. The hinge structure 17 and the drive member 19 are thus fixed relative to each other in the default state.

Figure 5A:
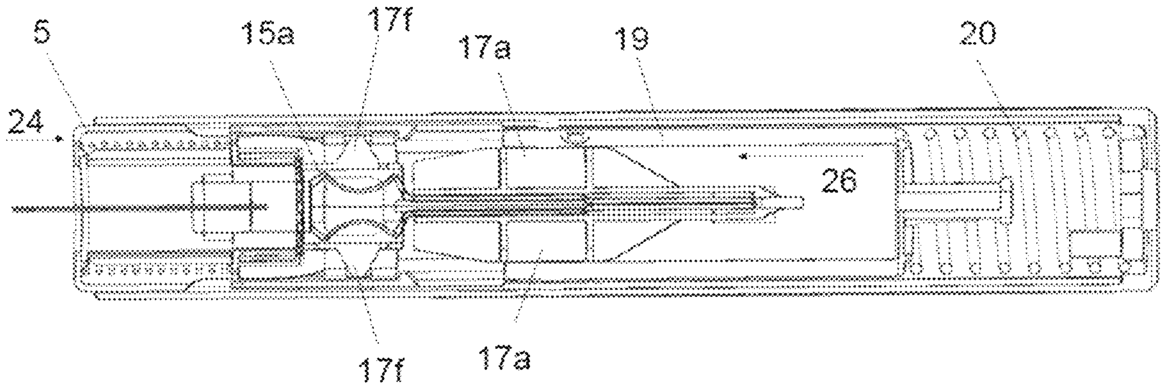
FIG. 5A is a sectional view of the medicament delivery device during a medicament delivery operation.

FIG. 5A shows the medicament delivery device 1 during a medicament delivery operation. The medicament delivery device 1 is pressed against the site of injection by the operator, causing the delivery member cover 5 to move from the first position to the second position, as illustrated by the arrow 24. The delivery member 22 is hence exposed, penetrating the tissue.

The distal movement of the delivery member cover 5 causes the cam surfaces 5*b* of the delivery member cover 5 to cooperate with a respective one of the radially outwards extending protrusions 19*a* of the drive member 19. This results in rotation of the drive member 19. The drive member 19 therefore disengages from the housing 3 and is moved in the proximal direction, as shown by arrow 26, due to the biasing by the distal resilient member 20. This proximal movement causes the drive member 19 to move over the hinge arms 17*a*, which are moved in the radial direction towards each other, discharging the content of the distal gas container 15*b* into the liquid container 15*a*, pushing the content of the liquid container 15*a* through the delivery member 22.

At the beginning of medicament expulsion, the liquid container 15*a* is pressurised enough by the liquid medicament to withstand the radially inwards directed force applied by the oppositely arranged radially outwards extending structures 17*f* which, being provided on the arms 17*e*, are urged radially inwards by the biasing force from the proximal resilient member 9 provided onto the proximal sleeve 11. Once the content of the liquid container 15*a* has been discharged, the liquid container 15*a* will not be sufficiently pressurised to withstand the radial pressure provided by the radially outwards extending structures 17*f*.

Figure 5B:
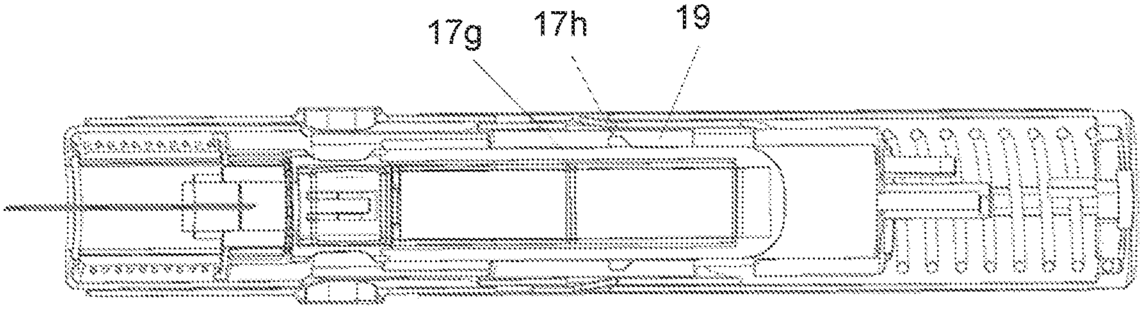
FIG. 5B is a sectional view of the medicament delivery device during a medicament delivery operation, the section being taken at 90 degrees angle relative to the section shown in FIG. 5A.

FIG. 5B shows a sectional view in a plane at 90 degrees angle relative to the sectional view shown in FIG. 5A. It can be seen that the protrusions 17*h* have been received by the drive member 19. The drawing is schematic, and in reality, the frame 17*g* would flex radially inwards and the protrusions 17*h* would bear against the inner surface of the drive member 19.

Figure 6:
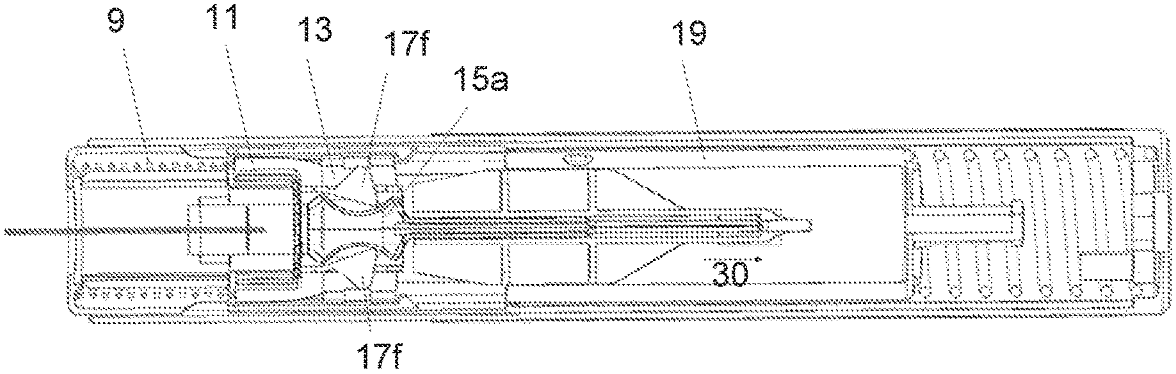
FIG. 6 is a sectional view of the medicament delivery device during medicament delivery, when arms collapse over a liquid container.

FIG. 6 shows the medicament delivery device 1 when the radially outwards extending structures 17*f* have collapsed over the liquid container 15*a* which has been emptied or essentially emptied of liquid. As a result, the hinge structure 17 is released from engagement with the holding sleeve 13. The proximal sleeve 11 will thus be moved in the distal direction, also moving the hinge structure 17 in the distal direction. The hinge structure 17 is thus moved further into the drive member 19, as shown by arrow 30, to obtain a final axial position. The hinge structure 17 also brings with it the medicament container structure 15, which is axially fixed relative to the hinge structure 17. The delivery member 22 is thus withdrawn into the housing 3, as shown in FIG. 7A, which shows a final state of the medicament delivery device 1, after use.

Figure 7A:
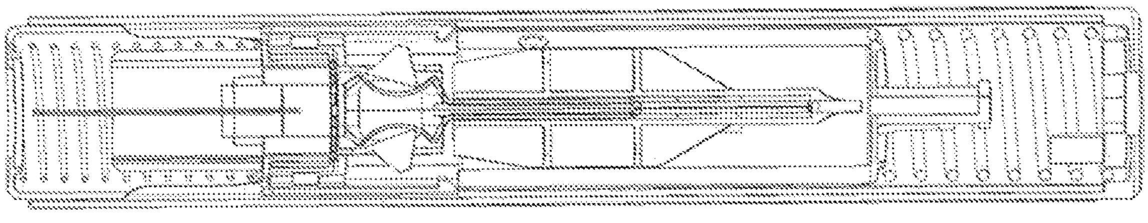
FIG. 7A is a sectional view of the medicament delivery in a final state after medicament delivery has been performed.
Figure 7B:
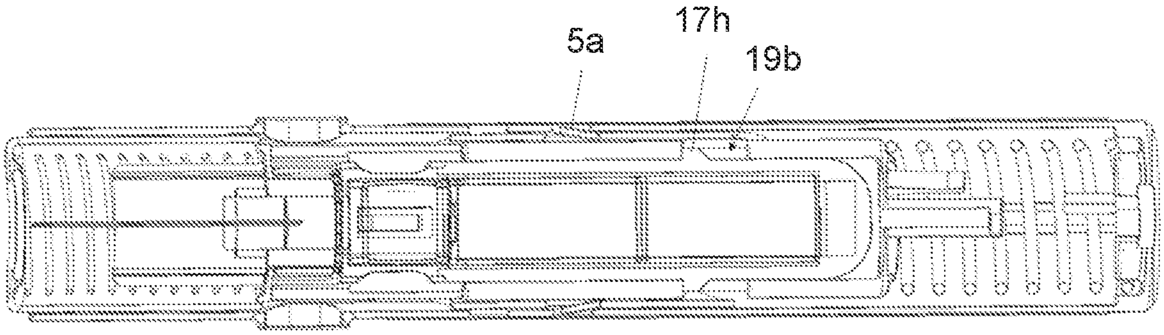
FIG. 7B is a sectional view of the medicament delivery device in the final state, the section being taken at 90 degrees angle relative to the section shown in FIG. 7A.

FIG. 7B shows a sectional view in a plane at 90 degrees angle relative to the sectional view shown in FIG. 7A. The protrusions 17*h* have engaged with the radial openings 19*b* of the drive member 19, axially interlocking the hinge structure 17 with the drive member 19. Moreover, the delivery member cover 5*a* is engaged with the second radial opening 3*d* of the housing 3. The delivery member cover 5*a* is thereby axially locked in the second position.

The medicament delivery device 1 may be disposed of in this final state, in which the delivery member 22 is protected inside the housing 3.

According to some variations, the drive member could for example be motor driven or manually driven instead of having an automatic spring-loaded structure. Moreover, it is envisaged that e.g. the hinge structure according to some examples could be provided without the radially outwards extending structures, and the medicament delivery device could thus be provided without the proximal sleeve and the holding sleeve.

The presently disclosed concept has mainly been described above with reference to a few examples. However, as is readily appreciated by a person skilled in the art, other embodiments than the ones disclosed above are equally possible within the scope of the presently disclosed concept, as defined by the appended claims.

The invention claimed is:

1. A medicament delivery device for expelling medicament from a mechanically flexible medicament container structure, the medicament delivery device comprising:
   a housing having a proximal end and a distal end;
   a hinge structure having two hinge arms, the hinge structure being arranged in the housing and configured to receive a portion of the medicament container structure between the two hinge arms; and
   a hollow drive member biased towards the proximal end and arranged distally relative to the hinge arms in the housing, the drive member having an inner diameter which is smaller than a radial dimension of the hinge arms;
   wherein the drive member is configured to be released from a first axial position during a medicament delivery operation and move towards the proximal end of the housing, causing the drive member to move radially over the hinge arms which thereby move radially inwards towards each other to mechanically deform the portion of the medicament container structure for expulsion of medicament.

2. The medicament delivery device as claimed in claim 1, wherein the hinge arms are directed towards the proximal end of the housing.

3. The medicament delivery device as claimed in claim 2, wherein each hinge arm has an end portion that tapers in a direction towards the distal end of the housing.

4. The medicament delivery device as claimed in claim 1, wherein the hinge structure is biased towards the distal end of the housing, and wherein the hinge structure has a frame provided with radially outwards extending protrusions configured to bear against a proximal end of the drive member for distancing the hinge arms from contact with the drive member when the drive member is in the first axial position.

5. The medicament delivery device as claimed in claim 1, comprising a distal resilient member configured to bias the drive member towards the proximal end of the housing.

6. The medicament delivery device as claimed in claim 1, wherein the mechanically flexible medicament container structure is a blow-fill-seal container.

7. A medicament delivery device for expelling medicament from a mechanically flexible medicament container structure having a proximal liquid container and a distal gas container in fluid communication with the liquid container, the medicament delivery device comprising:
   a housing having a proximal end and a distal end;
   a liquid container holder biased towards the distal end, the liquid container holder having a chamber configured to receive the liquid container, the liquid container holder having oppositely arranged radially flexible arms forming part of a respective side surface of the chamber, each arm having a radially outwards extending structure;
   an expulsion member configured to pressurize the gas container during a medicament delivery operation such that gas is expelled from the gas container into the liquid container to thereby expel liquid from the liquid container; and
   a holding sleeve arranged around the liquid container holder and being axially fixed relative to the housing;
   wherein the radially outwards extending structures are configured to be in contact with a respective radial surface of the holding sleeve to prevent the liquid container holder from moving axially towards the distal end, wherein the holding sleeve comprises radial openings, wherein each radial surface is formed by a distal end surface of a respective opening, wherein the arms are urged radially inwards against the liquid container by the biasing and the contact with the radial surfaces of the holding sleeve, wherein the arms are subjected to a radially outwards directed counter-pressure by the liquid container when the liquid container is filled with liquid, and wherein the arms are configured to move radially inwards when the liquid container is emptied and its internal pressure is reduced, causing the radially outwards extending structures to be released from contact with the radial surfaces of the holding sleeve and the liquid container holder to move towards the distal end inside the housing and obtain a final axial position.

8. The medicament delivery device as claimed in claim 7, wherein the radially outwards extending structures and/or the radial surfaces define inclined surfaces relative to a radial plane of the housing to facilitate radial inwards movement of the arms.

9. The medicament delivery device as claimed in claim 7, comprising a proximal sleeve, and a proximal resilient member biasing the proximal sleeve against the liquid container holder in a direction towards the distal end of the housing, thereby biasing the liquid container holder towards the distal end of the housing.

10. The medicament delivery device as claimed in claim 7, comprising a hinge structure having two hinge arms, the hinge structure being arranged in the housing and configured to receive the gas container between the two hinge arms, wherein the liquid container holder forms a proximal end of the hinge structure, wherein the expulsion member is a hollow drive member biased towards the proximal end and arranged distally relative to the hinge arms in the housing, the drive member having an inner diameter which is smaller than a radial dimension of the hinge arms, wherein the drive member is configured to be released from a first axial position during a medicament delivery operation and move towards the proximal end of the housing, causing the drive member to move radially over the hinge arms which thereby move radially inwards towards each other to mechanically deform the gas container.

11. The medicament delivery device as claimed in claim 10, wherein the hinge structure has a radially flexible frame provided with radially outwards extending protrusions configured to bear against a proximal end of the drive member for distancing the hinge arms from contact with the drive member when the drive member is in the first axial position, the drive member having radial openings configured to interlock with a respective one of the protrusions when the liquid container holder has reached its final axial position.

12. The medicament delivery device as claimed in claim 7, wherein the mechanically flexible medicament container structure is a blow-fill-seal container.

13. A medicament delivery device comprising:

a housing having a proximal end and a distal end;

a mechanically flexible medicament container positioned within the housing;

a hinge structure comprising two hinge arms that surround part of the medicament container;

a spring; and a hollow drive member biased by the spring towards the proximal end, where the two hinge arms are positioned within the drive member such that outer surfaces of the hinge arms with engage with an inside surface of the drive member during delivery of medicament from the medicament container when the drive member is released from a first axial position.

14. The medicament delivery device of claim 13, wherein each hinge arm has an end portion that tapers in a direction towards the distal end of the housing and are biased by the spring towards the distal end of the housing.

15. The medicament delivery device of claim 13, wherein axial movement of the drive member causes the hinge arms to move radially inwards towards each other to mechanically deform the portion of the medicament container.

16. The medicament delivery device of claim 13 further comprising a distal gas container in fluid communication with the medicament container.

17. The medicament delivery device of claim 16, wherein the hinge structure further comprises a radially flexible frame provided with radially outwards extending protrusions configured to bear against a proximal end of the drive member for distancing the hinge arms from contact with the drive member when the drive member is in the first axial position, the drive member having radial openings configured to interlock with a respective one of the protrusions when the medicament container holder has reached a final axial position.

* * * * *